United States Patent [19]

Koning et al.

[11] Patent Number: 4,566,456
[45] Date of Patent: Jan. 28, 1986

[54] APPARATUS AND METHOD FOR ADJUSTING HEART/PACER RATE RELATIVE TO RIGHT VENTRICULAR SYSTOLIC PRESSURE TO OBTAIN A REQUIRED CARDIAC OUTPUT

[75] Inventors: Gerrit Koning, Vries, Netherlands; Edward A. Schroeppel, Miramar, Fla.

[73] Assignee: Cordis Corporation, Miami, Fla.

[21] Appl. No.: 662,277

[22] Filed: Oct. 18, 1984

[51] Int. Cl.$^4$ ............................................. A61N 1/36
[52] U.S. Cl. .............................. 128/419 PG; 128/675
[58] Field of Search ...... 128/419 P, 419 PG, 673–675

[56] References Cited

U.S. PATENT DOCUMENTS

| | | | |
|---|---|---|---|
| 2,634,721 | 4/1953 | Greenwood, Jr. | 128/2.05 |
| 2,976,865 | 3/1961 | Shipley | 128/2.05 |
| 3,088,323 | 5/1963 | Welkowitz et al. | 73/398 |
| 3,294,988 | 9/1964 | Packard | 310/8 |
| 3,358,690 | 12/1967 | Cohen | 128/419 |
| 3,593,718 | 7/1971 | Krasner | 129/419 P |
| 3,650,277 | 3/1972 | Sjostrand et al. | 128/419 C |
| 3,815,611 | 6/1974 | Denniston, III | 128/419 D |
| 3,828,371 | 8/1974 | Purdy | 3/1 |
| 3,857,399 | 12/1974 | Zacouto | 128/419 P |
| 4,009,721 | 3/1977 | Alcidi | 128/419 PG |
| 4,140,132 | 2/1979 | Dahl | 128/419 PG |
| 4,191,193 | 3/1980 | Seo | 128/675 |
| 4,201,219 | 5/1980 | Gonzalez | 128/419 PG |
| 4,202,339 | 5/1980 | Wirtzfeld et al. | 128/419 PG |
| 4,228,803 | 10/1980 | Rickards | 128/419 PG |
| 4,313,442 | 2/1982 | Knudson et al. | 128/419 PG |
| 4,428,378 | 1/1984 | Anderson et al. | 128/419 PG |
| 4,432,372 | 2/1984 | Monroe | 128/675 |
| 4,436,092 | 3/1984 | Cook et al. | 128/419 PG |
| 4,485,813 | 12/1984 | Anderson et al. | 128/419 P |

FOREIGN PATENT DOCUMENTS 858843 9/1981 U.S.S.R. .

OTHER PUBLICATIONS

Cohen "A Theoretical Right Atrial Pressure Feedback Heart Rate Control to Restore Physiologic Control to the Rate-Limited Heart" PACE Jul.–Aug. 1984, vol. 7, pp. 671–677.

Primary Examiner—William E. Kamm
Assistant Examiner—Mitchell J. Shein
Attorney, Agent, or Firm—Henry W. Collins; Thomas R. Vigil

[57] ABSTRACT

The apparatus for pacing a heart in accordance with the heart rate needed to produce a required cardiac output while the person is exercising, comprises a pacer adapted to be implanted in a human body and having a pulse generator and control circuitry (e.g. including a microprocessor) therein, a pacing lead adapted to be implanted in a heart and having a distal electrode adapted to engage and supply pacing pulses to a right ventricle of a heart and, a pacer sensor for sensing right ventricular systolic pressure mounted on the lead. An algorithm and routine utilizing same are stored in the control circuitry (microprocessor) and are adapted to relate right ventricular systolic pressure and/or the time derivative of the pressure sensed with the required heart rate needed to supply a desired cardiac output and to cause the pacer to pace the heart at the required heart rate when the heart is not naturally paced.

29 Claims, 19 Drawing Figures

APPARATUS AND METHOD FOR ADJUSTING HEART/PACER RATE RELATIVE TO RIGHT VENTRICULAR SYSTOLIC PRESSURE TO OBTAIN A REQUIRED CARDIAC OUTPUT

BACKGROUND OF THE INVENTION

1. Field of the Invention

The present invention relates to a pacer system which is adapted to alter the rate of the pacer pulses delivered (rate of pacing pulses delivered by an artificial pacemaker) to the heart while an individual is exercising utilizing the systolic pressure or its time derivative sensed in the right ventricle to obtain a required cardiac output.

2. Description of the Prior Art

Heretofore patients with heart dysfunctions or heart disease such as sinus node disease have been able to live a relatively normal life with the implantation of an artificial pacemaker often referred to as a pacer. However, such pacers have not always been able to mimic the response of a normal healthy heart. A normal heart responds to exercise and stress by increasing cardiac output through increased heart rate or stroke volume.

In this respect, patients with sinus node disease have lost the ability to increase heart rate with exercise. Accordingly, it has become a goal of optimal pacing to provide exercise responsiveness in a pacer by sensing the need for increased cardiac output.

With a view toward obtaining this goal, a number of pacemakers have been proposed for indirectly sensing the need for increased heart rate by sensing P-waves, nerve impulses, Q-T interval, pH, oxygen saturation, respiratory rate, stroke volume, motion, atrial pressure and temperature.

A P-wave triggered artificial pacemaker adapted to be exercise responsive by responding to average atrial rate has been proposed in the Knudson & Amundson U.S. Pat. No. 4,313,442.

An artificial pacemaker responsive to changes in the Q-T interval is proposed in the Rickards U.S. Pat. No. 4,228,803.

A proposal for placing electrodes on the Hering's nerve that originate from receptors in the sinus and glomus carotids is disclosed in the Gonzalez U.S. Pat. No. 4,201,219.

Pacers for sensing blood pH are proposed in the Alcidi U.S. Pat. No. 4,009,721 and the Mauer et al U.S. Pat. No. 4,252,124.

An artificial pacemaker that senses oxygen saturation at the tip of a catheter in the right ventricle is proposed in the Wirtzfeld et al U.S. Pat. No. 4,202,339.

Another artificial cardiac pacemaker which increases pacing rate in accordance with an increase in respiration rate is proposed in the Krasner U.S. Pat. No. 3,593,718.

Pacers for sensing motion or mechanical activity are proposed in the Dahl U.S. Pat. No. 4,140,132 and the Anderson et al U.S. Pat. No. 4,428,378.

Another artificial cardiac pacemaker responsive to exercise by sensing venous blood temperature in the right ventricle of the heart is proposed in Cook et al U.S. Pat. No. 4,436,092.

In a healthy heart, the sympathetic nervous system activates the sinus node to increase its frequency. Secondly, it activates the heart to increase its dynamic contraction during exercise. The first activation is lost in patients with sinus node disease but the second phenomenon of dynamic contraction still exists. This means that exercise modified increased sympathetic activity can be detected by measuring the right ventricular systolic pressure. As will be described in greater detail hereinafter, the apparatus of the present invention utilizes the right ventricular systolic pressure or the time derivative thereof to control the pacing rate of an implanted artificial pacemaker.

Heretofore it has been proposed to sense pressure in the right atrium and to utilize the pressure sensed to control pacing of an electrode in the right ventricle in the Cohen U.S. Pat. No. 3,358,690.

Also, the Zacouto U.S. Pat. No. 3,857,399 discloses, in FIG. 19 thereof, a pressure sensor that measures either left ventricular pressure or intramyocardial pressure. One sensor is located in the myocardium or septum and the other sensor is located in the left ventricle. Apparently, the pacer coupled to these sensors responds to average base pressure over relatively long periods of time and the pacer system disclosed therein appears to be static and slowly responsive to exercise.

In the field of artificial hearts, it has been proposed in the Purdy U.S. Pat. No. 3,828,371 directed to a self contained artificial heart, to control operation of the artificial heart relative to the sensing of atrial pressure.

Further, there is disclosed in U.S.S.R. Inventor's Certificate No. 858,843 a device for controlling a prosthesis of the heart which replaces a natural heart and which comprises a servomechanism responsive to blood pressure in the atrium of the heart.

The apparatus of the present invention can utilize a piezoresistive pressure sensor for sensing right ventricular systolic pressure and a number of different piezoresistive pressure sensors for use in measuring blood pressure have been proposed. Also other blood pressure sensing devices or blood pressure operated devices have been proposed. See for example the pressure sensors and transducers disclosed in the following U.S. patents:

| U.S. PAT. NO. | PATENTEE |
| --- | --- |
| 2,634,721 | Greenwood, Jr. |
| 2,976,865 | Shipley |
| 3,088,323 | Welkowitz et al |
| 3,294,988 | Packard |
| 3,563,245 | McLean |
| 3,906,960 | Lehr |
| 4,432,372 | Monroe |
| Published European Patent Application | |
| 0 080 347 to | Anderson et al |

The apparatus of the present invention differs from the previously proposed apparatus by providing an implanted artificial pacemaker having a microprocessor therein with a program or algorithm stored in the microprocessor for controlling the pacing rate of pacing pulses supplied to an electrode at the end of a pacing lead in the right ventricle relative to, and in response to, the right ventricular systolic pressure or the time derivative thereof obtained from a pressure sensor mounted on the pacing lead and located in the right ventricle.

SUMMARY OF THE INVENTION

According to the present invention, there is provided an apparatus for pacing a heart in accordance with the heart/pacer rate needed to produce a required cardiac output while the person is exercising, comprising:
a pacer adapted to be implanted in a human body and having a pulse generator and control circuitry which may be realized by a microprocessor therein;
a pacing lead adapted to be implanted in a heart and having a distal electrode adapted to engage and supply pacing pulses to a right ventricle of a heart;
pressure sensing means mounted on said pacing lead for sensing right ventricular systolic pressure; and
means, including said control circuitry for relating the right ventricular systolic pressure and/or the time derivative thereof with the required rate needed to supply a desired cardiac output and for causing said pacer to pace the heart at the required rate when the heart is not naturally paced.

Further according to the invention, there is provided a method for pacing a heart in accordance with the heart rate needed to produce a required cardiac output while the person is exercising, comprising the steps of:
sensing right ventricular systolic pressure;
relating the right ventricular systolic pressure and/or the time derivative thereof with the required heart rate needed to supply a desired cardiac output; and
pacing the heart at the required heart rate when the heart is not naturally paced.

DESCRIPTION OF THE PREFERRED EMBODIMENTS

Figures 1, 2:
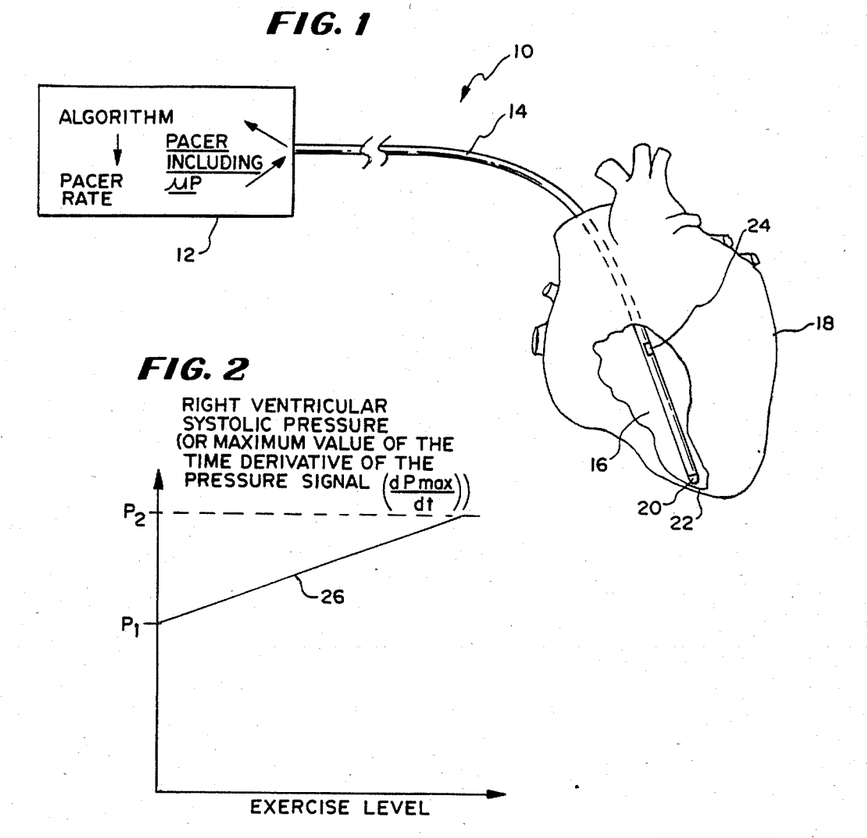
FIG. 1 is a block mechanical and schematic diagram of the apparatus of the present invention for controlling the pacing rate of an implanted artificial pacemaker in response to the right ventricular systolic pressure or time derivative thereof in accordance with the teachings of the present invention and shows a pacing lead with a pacing electrode thereof located at the apex of the right ventricle, a pressure sensor mounted on the pacing lead and positioned in the right ventricle and a pacer containing a microprocessor and control circuitry for controlling the pacing rate in response to the pressure sensed or the time derivative thereof.
FIG. 2 is a graph of the right ventricular systolic pressure or value of the derivative of the right ventricular pressure signal versus exercise level.

Referring now to the drawings in greater detail, there is illustrated in FIG. 1 an apparatus 10 or pacer system 10 which is constructed according to the teachings of the present invention and which includes an implanted pacer or artificial pacemaker 12 shown in schematic form. The pacer 12 has therein a pulse generator comprising amplifiers to sense electrical cardiac activity, excitation and detection circuit for the pressure sensor, and control circuitry ($\mu$P). A pacing lead 14 is connected to the pacer 12 at the proximal end thereof and extends pervenously into the right ventricle 16 of a heart 18 where an electrode 20 at the distal end thereof engages and stimulates the apex 22 of the right ventricle. A pressure sensor 24 is mounted on the lead 14 so as to be located in the right ventricle just below the tricuspid valve and is connected to the sensor-excitation/amplifier detection circuitry in the pacer 12.

When a patient with sinus node disease has a pacing system implanted within his or her body with a pacing lead 14 implanted in a ventricle of the heart, particularly the right ventricle, such pacing system 10 stimulates the ventricle at a preset rate. In patients with sinus node disease the heart has lost the ability to increase ventricular rate with exercise. However, the heart continues to increase its dynamic contraction.

In accordance with the teachings of the present invention, the right ventricular systolic pressure is sensed by the pressure sensor 24 and this pressure, namely the peak pressure sensed or the time derivative of the pressure, is used for controlling the rate of application of pulses to the electrode 20 which rate is referred to as the pacer rate.

In other words, the right ventricular systolic pressure is used as a measure of exercise level. Every exercise level has its corresponding heart rate. Thus, based on the pressure related to exercise level, i.e., the peak right ventricular systolic pressure or the time derivative thereof, the appropriate heart/pacer rate can be determined. In this way, a pacer 12 can be adapted to exercise. More specifically, the rate of pulse generation or pacer rate can be controlled so that the pacing system 10 can be adapted for exercise when an individual engages in exercise.

As shown in FIG. 2, the right ventricular systolic pressure value of the time derivative of the pressure signal (dPmax/dT) during the time of exercise will increase from some lower level $P_1$ at zero exercise to an upper level $P_2$ at maximum exercise level along a generally linear slope 26 of the graph of the right ventricular systolic pressure (or value of the time derivative of the pressure signal) versus exercise level shown in FIG. 2.

Figure 3:
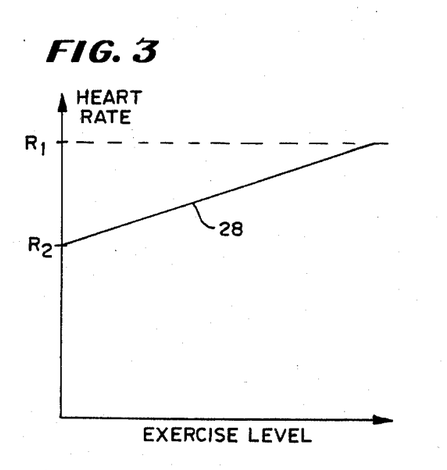
FIG. 3 is a graph of heart rate versus exercise level.

At the same time in a normal heart, as shown in FIG. 3, the heart rate will increase from a lower rate $R_1$ at zero exercise to an upper level of heart rate $R_2$ along a generally linear slope 28 of the graph of heart rate versus exercise level shown in FIG. 3.

Figure 4:
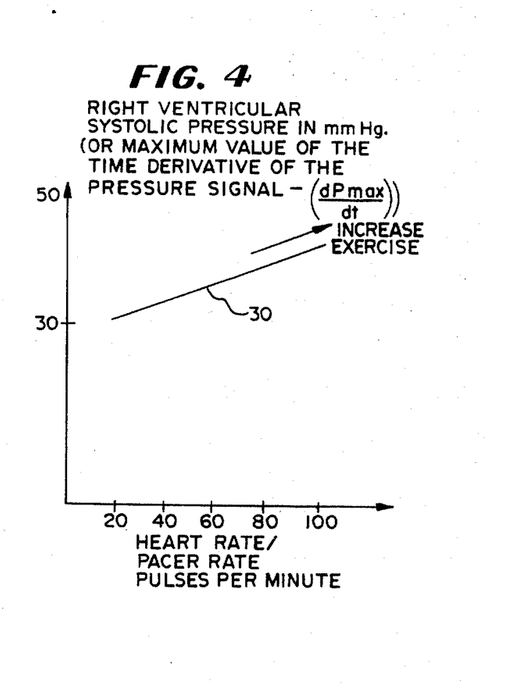
FIG. 4 is a graph of right ventricular systolic pressure or value of the derivative of the pressure signal versus the heart rate or the pacer rate.

Thus, it will be appreciated that the frequency of the heart rate of a normal heart can be correlated to the right ventricular systolic pressure while an individual is exercising and such correlation is generally linear as shown by the slope 30 of the graph of right ventricular systolic pressure (or the value of the time derivative thereof) versus heart rate or pacer rate shown in FIG. 4.

As will be described in greater detail hereinafter, this relationship between the change in pressure to the change in the frequency in heart rate for a normal heart can be programmed in the form of an algorithm in the memory of the microprocessor or any other control circuitry mounted within the pacer 12. Thus, the apparatus or pacing system 10 can utilize the pressure sensed by the pressure sensor 24 to adjust the pacer rate according to the algorithm stored in the memory of the microprocessor within the pacer 12 which relates right ventricular systolic pressure to the required frequency of heart contractions or pacer rate.

For this purpose, the system 10 requires the pressure sensor 24 in the implanted pacing lead 14 and electronic circuitry in microprocessor based pacer 12 for calculating the required change in rate based on the pressure change and the algorithm stored in the memory to cause the control circuitry to change the pacer rate.

The correlation of the change in right ventricular systolic pressure (or value of the time derivative of the pressure signal) versus change in heart rate is shown in FIG. 4.

It may be preferable to use the time derivative of the pressure signal (dP/dT) instead of the pressure itself. For this purpose, the pacer 12 will have a differentiating circuit or algorithm incorporated therein. Use of the time derivative of the pressure signal avoids DC drift because dP/dT is an AC signal. Furthermore, combining pressure sensing and the time derivative (dP/dT) results in a redundant and therefore more reliable system.

The pressure sensor 24 can be defined or realized by a number of different types of pressure sensing elements. For example, the pressure sensor may be a hermetically sealed absolute strain gauge transducer or a capacitive pressure transducer or any type of piezoresistive transducer.

Also a fiber optic type pressure sensor can be utilized.

Figure 5:
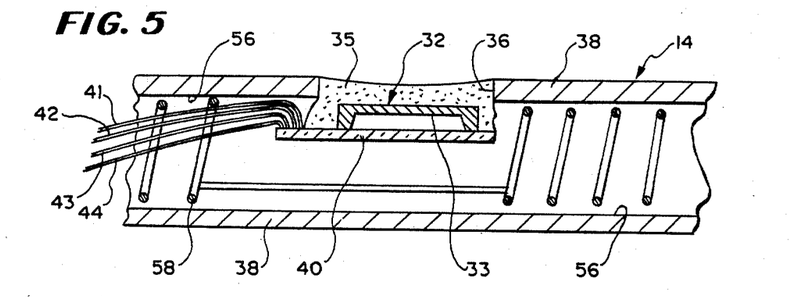
FIG. 5 is a longitudinal sectional view of a portion of the pacing lead shown in FIG. 1 with portions broken away and shows a pressure sensitive piezoresistive microelectronic transducer mounted in the wall of the pacing lead.

In one preferred embodiment of the apparatus 10 of the present invention, the pressure sensor 24 is realized by a piezo-resistive microelectronic transducer 32 on a chip 33 which is embedded within an elastomeric material 35 that is secured within an opening 36 in a tubular sheath 38 of the lead 14. Typically, the transducer 32 is mounted on a glass carrier 40 and four insulated sensor wire conductors 41–44 are coupled to the glass carrier for connection to the transducer 32.

The four wire conductors 41–44 are connected to a bridge 46 (FIG. 9) comprised of variable piezo-resistors 51–54 (FIG. 9) of the transducer 32.

The conductors 41–44 are shown extending in an interior lumen 56 of the sheath 38 and more particularly through a cylindrical envelope defined within a coiled conductor 58 which is connected between the pacer 12 and the distal tip electrode 20. Preferably, the sensor wire conductors 41–44 are arranged so as not to obstruct the envelope defined by the coil 58 provided for a stylet for locating the distal electrode 20 at the distal end of the lead 14. For this purpose, the insulated wire conductors 41–44 can be coiled with and between coils of the coiled conductor 58.

Alternatively, the sensor wire conductors 41–44 can be mounted in a small teflon tubing and float in the lumen or space defined within the coiled conductor 58.

A still further alternative is to place the sensor wire conductors 41–44 between the coiled conductor 58 and the tubular sheath 38.

Figures 6, 7, 8:
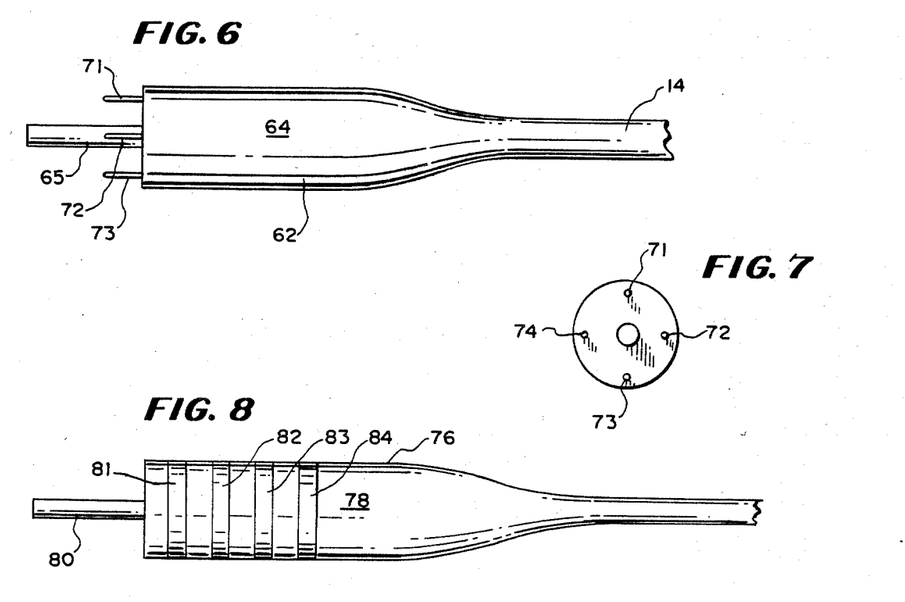
FIG. 6 is a side longitudinal view of the proximal terminal electrode assembly of the pacing lead shown in FIG. 1 and shows a central terminal pin and four sensor pins.
FIG. 7 is an end view of the terminal electrode assembly shown in FIG. 6.
FIG. 8 is a side longitudinal view of still another proximal terminal electrode assembly and shows a central pin electrode at the proximal end of the assembly and four spaced apart ring electrodes on the cylindrical body of the terminal electrode assembly.

In order that the sensor wire conductors 41–44 are connected to appropriate connector terminals in the pacer 12, a terminal electrode assembly 62 at the proximal end of the pacing lead 14 is provided with a generally cylindrical body 64 having a central cathodic terminal pin 65 and four terminal pins 71–74 extending rearwardly therefrom as shown in FIGS. 6 and 7. These sensor terminal pins 71–74 are received in appropriate sockets within the pacer 12.

Alternatively, instead of sensor pins 71–74 a proximal terminal electrode assembly 76 having a generally cylindrical body 78 can be provided with a central cathode terminal pin 80 extending rearwardly from the body 78 and four ring electrodes 81–84 spaced apart on the outer periphery of the cylindrical body 78 as shown in FIG. 8.

Figure 9:
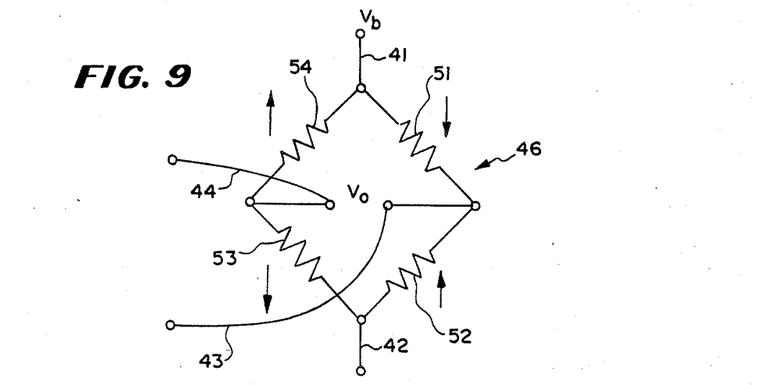
FIG. 9 is a schematic circuit diagram of the bridge circuit of the piezoresistive microelectronic transducer shown in FIG. 5.

As is typical of piezo-resistive transducers, the transducer 32 comprises the four resistors 51–54 electrically connected in a bridge circuit 46 as shown in FIG. 9. A voltage is applied across two corners of the bridge via sensor wire conductors 41 and 42. Then, the voltage across the other two corners of the bridge, namely voltage $V_0$ is sensed by sensor wire conductors 43 and 44.

Initially, without any pressure placed on the transducer 32 the voltage $V_0$ will be zero. However, when pressure is placed on the transducer 32, the resistance of resistors 51 and 53 will go down and the resistance of resistors 52 and 54 will go up. This will cause a change in the value of the voltage $V_0$ across the other two corners of the bridge 46, which voltage $V_0$ is supplied via sensor wire conductors 43 and 44 to the pacer 12 of the apparatus 10 as an indication of a change in right ventricular systolic pressure.

Typically, a pressure sensor 24 having an impedance of approximately 1k ohm requires 1–5 volt excitation which translates to approximately 1–5 ma. current flow. This is too much current drain for the battery power source for the pacemaker 12. Accordingly, to reduce the current drain, voltage and current pulses with a 1:200 duty cycle are utilized and supplied to and received from the bridge circuit 46 whereby the current drain is reduced to an acceptable value of approximately 5 microamps. In this way, with voltage pulses having a duty cycle of 1:200 the pressure applied to the transducer 32 of the pressure sensor 24 is only sampled periodically. Then, of course, the sampling frequency relative to pulse duration has to be chosen in such a way as to minimize current drain and still yield a reproducible pressure curve such as by utilizing the Shannon-Nyguist theorem of sampling.

With reference to FIG. 4, at the onset of exercise, the right ventricular systolic pressure will vary with heart rate or pacer rate. The first step in utilizing the apparatus 10 involves sensing of the right ventricular systolic pressure. Next the peak of the pressure is detected.

To avoid small oscillations a general filtering principle or an N-point averaging technique is employed. In this respect, an N number of samples between 1 and 10, for example, are made and the average is chosen as the sampled peak pressure. Then, this average is compared with the previously stored average of the peak pressure value to determine whether there has been a change. The change is detected by measuring $\Delta P = P_x - (P_{x-1})$ where x equals the time order for a number of samples, N. Of course to make this detection more reliable, one would detect, sense and determine $P_x - (P_{x-1})$, $P_x - (P_{x-2})$ and $P_x - (P_{x-3})$. As a simplification, when all the differences have the same sign, the change is consistent. Then $\Delta P = P_x - (P_{x-1})$ and that is used as an input for the algorithm stored in the microprocessor within the pacer 12.

The algorithm or routine in its most simple form relates $\Delta R$, which is the change in rate of pulses emitted by the pacer 12, literally to $\Delta P$, which is the pressure change. This can be realized in analog techniques but can also be realized in a digital manner using a so-called "look-up" table. The signal $\Delta P$ serves as an input to the microprocessor in the pacer 12 which serves to change the pacer rate frequency as a function of $\Delta P$. Typically, an algorithm relationship of $\Delta P$ to $\Delta R$, such as shown in FIG. 4, is stored in the memory of the microprocessor in the pacer 12 and provides the algorithm, i.e., slope 30, and the equation therefor, which is utilized by the control circuitry.

In the event the sensor 24 or the circuitry within the pacer 12 malfunctions, the control circuitry can be caused to exit the program or routine and convert the pacer to its standard non-exercise responsive function. Furthermore, if the peak pressure shows oscillation, the number N in the N-point averaging can be programmed or changed to a higher value and the circuitry for sensing or detecting a change in pressure can be programmed to take more samplings of differences before it decides that a change pressure, $\Delta P$, has occurred to cause a change in $\Delta R$.

It is important to note that according to the teachings of the present invention right ventricular systolic pressure values are utilized, and not diastolic pressure values. In other words, the right ventricular systolic pressure or the time derivative of the right ventricular systolic pressure is used as an indicator of exercise and the rate of the artificial pacemaker or pacer 12 is correlated to this change in right ventricular systolic pressure. The advantage of utilizing right ventricular systolic pressure resides in the fact that the change in right ventricular systolic pressure or the time derivative thereof is directly proportional to the sympathetic or exercise activity. That is to say, in a normal human being, right ventricular systolic pressure appears to be directly proportional to exercise without any time lag. This has the advantage over metabolic changes such as pH, oxygen saturation, etc., all of which occur at a time subsequent to the onset of exercise. Therefore, by utilizing the right ventricular systolic pressure or the time derivative thereof, a pacer directly follows exercise rather than lagging exercise.

Figure 10:
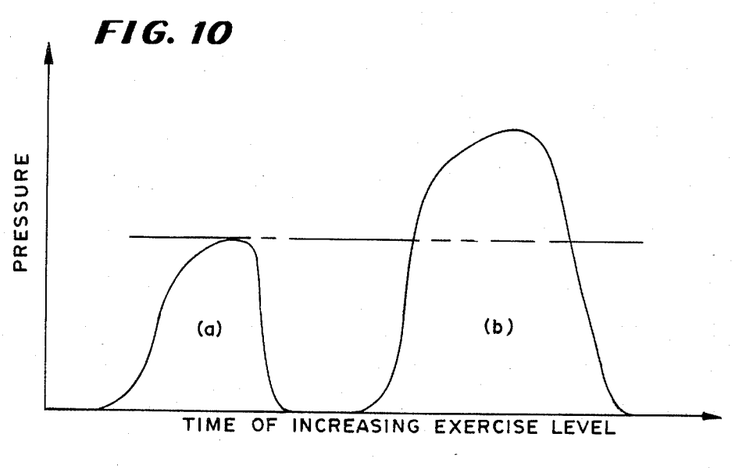
FIG. 10 is a graph of systolic right ventricular pressure versus time of increasing exercise level for two heart beats and shows the increase in pressure from one heart beat to another as an individual is starting to exercise.
Figure 11:
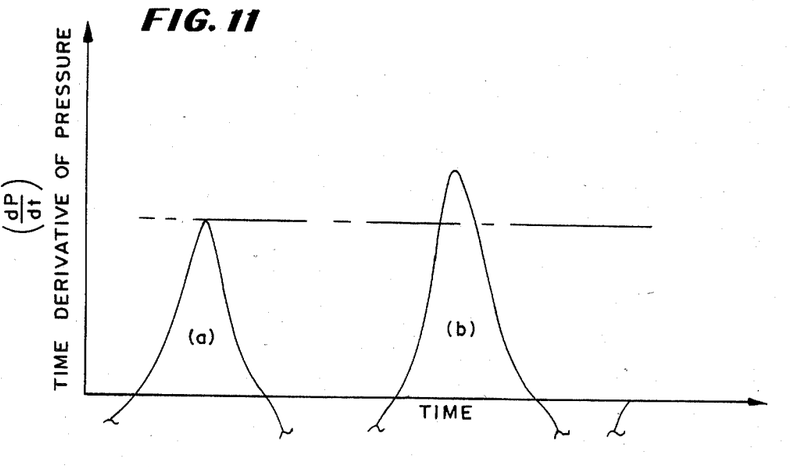
FIG. 11 is a graph of the time derivative of pressure in the right ventricle versus time for each of the pressure pulses shown in FIG. 10.

Referring now to FIG. 10, the theory behind the teachings of the present invention is readily shown by comparing waveforms "a" and "b" of the change in right ventricular systolic pressure as exercise is commenced. Clearly, the waveform "b" is greater than waveform "a" showing that there has been an increase in the right ventricular systolic pressure. The time derivative of the pressure waveform "a" and "b" shown in FIG. 10 is shown in FIG. 11. Here it is clear one can also compare the derivative of the peak pressure of pressure waveform "a" with the derivative of the peak pressure of the pressure waveform "b" and on the basis of the differences therebetween, cause a change in $\Delta R$.

Figure 12:
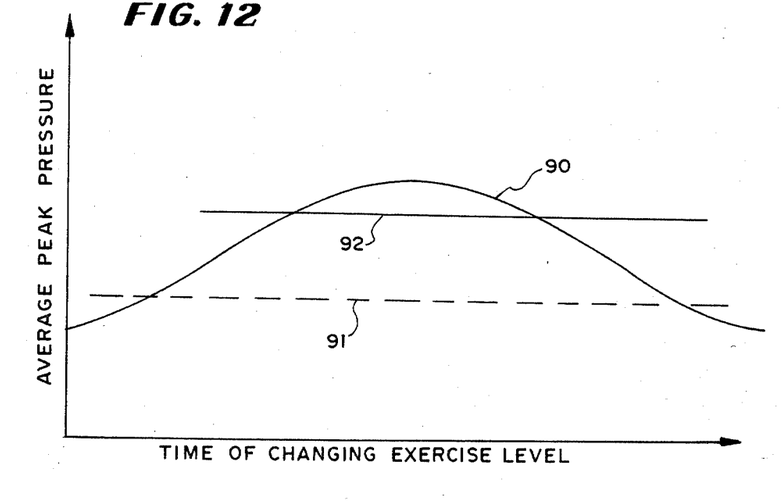
FIG. 12 is a graph of average peak pressure over time of changing exercise level from a period at the beginning of exercise to a period after exercise has been discontinued.

FIG. 12 shows the change in average peak pressure of the right ventricular pressure versus time of changing exercise level.

One can determine from a graph of changes in average peak pressure from a time before exercise to a time after exercise has been discontinued such as shown in FIG. 12 when the right ventricular systolic pressure has started to decrease in value. Thus, one can follow the curve 90 in FIG. 12 of change in average peak pressure versus time of exercise through and above some arbitrary peak values 91 and 92 of pressure. When the pressure exceeds value 91, the pacing rate has to be increased proportional with pressure. When the pressure goes lower than value 92, the pacing rate can be reduced commensurate with the relaxation of the heart and body after exercise has been discontinued.

Figure 13:
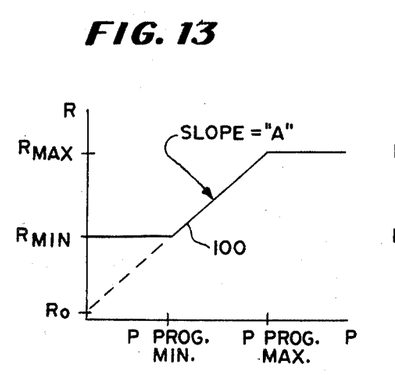
FIG. 13 is a graph of pacer rate versus pressure and shows the linear relationship between the pacer rate and the pressure between programmed minimum and maximum rates.

In utilizing the apparatus 10 as shown in FIG. 1, certain parameters have to be determined experimentally and programmed into the microprocessor within the pacer 12. First of all, as shown in FIG. 13, the linear relationship between heart rate and pressure (right ventricular systolic pressure) between a programmed minimum $P_{Prog.Min.}$ and a programmed maximum $P_{Prog.Max.}$ of heart rates is established and can be shown as graph or line 100 having a slope of this "A". The equation for the line 100 with the slope "A" is $$R_T = A(P_T - P_{T-1}) + (R_{T-1}).$$

This formula or algorithm is then utilized in the routine or program carried out by the microprocessor in the pacer 12. This routine is set forth in the flow chart shown in FIG. 15. According to this routine, the heart pacing rate and pressure values stored in the pacer 10 are constrained to vary along the line 100 delineated by the above equation having the slope "A". That is to say, even if the measured pressure $P_T$ exceeds the programmed maximum pressure, $P_{Prog.Max.}$, that value of $P_T$ will be stated as $P_{Prog. Max.}$.

Figure 15:
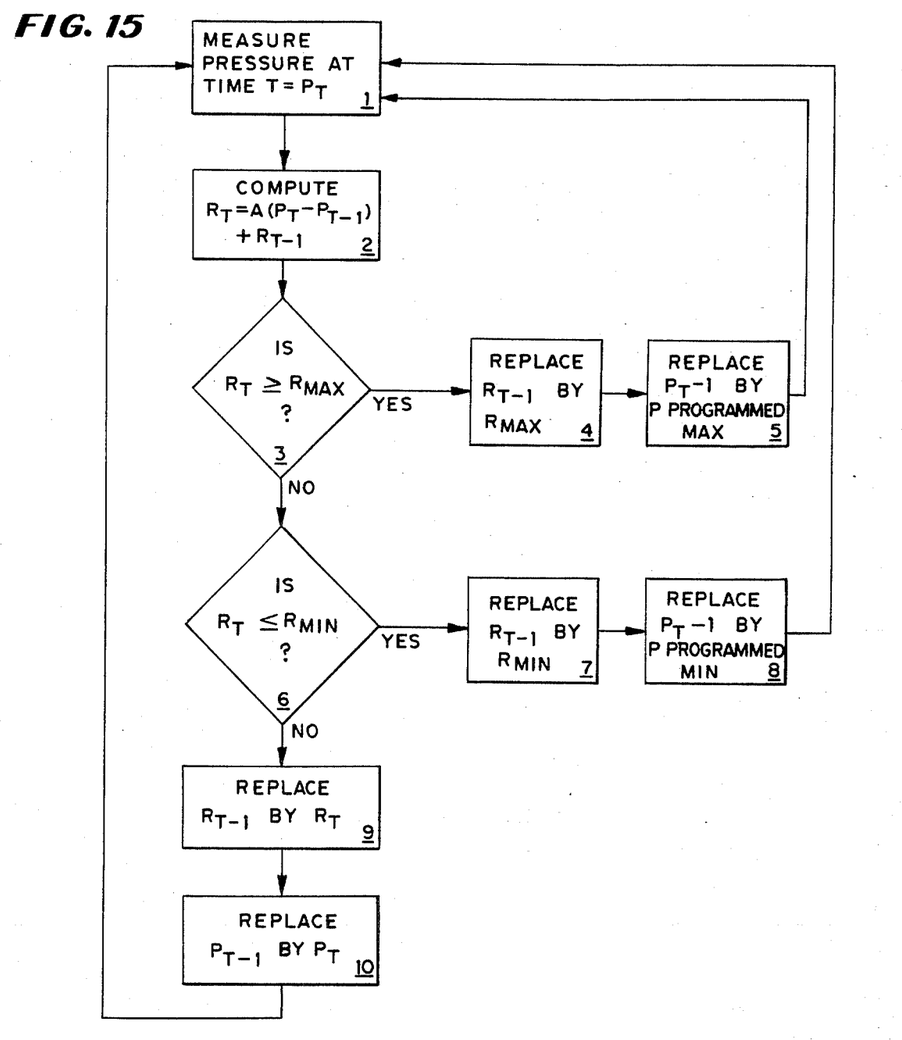
FIG. 15 is a flow chart of the program or routine carried out by the microprocessor of the apparatus shown in FIG. 1.

The steps carried out by the program or routine shown in FIG. 15 are as follows:

STEP 1. Here pressure is measured at the present time T and defined as $P_T$.

STEP 2. Here $R_T$ is calculated. If $P_T - (P_{T-1})$ is positive, $R_T$ will be larger than $R_{T-1}$. If negative, it will be smaller.

STEP 3. The pacer rate will only be changed to values on the sloped portion of the graph 100 as shown in FIG. 13. At STEP 3, a determination is made whether or not the value for the pacer rate will be at the extremes of the line or graph 100.

STEP 4. If $R_T$ is equal to or greater than $R_{Max.}$, then the pacer is programmed to $R_{Max.}$ and this value is stored as $R_{T-1}$.

STEP 5. Next the stored pressure is stored as $P_{Prog.Max.}$ and the routine loops back to STEP 1.

STEP 6. If $R_T$ is less than $R_{Min.}$, then the program goes on to STEP 6 where it is determined whether or not $R_T$ is equal to or less than $R_{Min.}$.

STEP 7. If $R_T$ is equal to or less than $R_{Min.}$, the microprocessor is caused to program the pacer to $R_{Min.}$ and stores that value as $R_{T-1}$.

STEP 8. Next, $P_{T-1}$ is stored as $P_{Prog. Min.}$ in the memory of the microprocessor.

STEP 9. If the microprocessor reaches this step, it means that $R_T$ is somewhere on the slope portion of the graph or line 100. The pacer is then programmed to R.

STEP 10. Next, at STEP 10, $P_{T-1}$ is replaced by $P_T$ and the microprocessor loops back to STEP 1.

It is to be noted that in most pacers the actual value programmed into a microprocessor would be the closest programmable value to $R_T$. However, $R_{T-1}$ is a calculated number. Again after $R_{T-1}$ has been replaced by the closest programmable value of $R_T$ and $P_{T-1}$ has been replaced by $P_T$, the microprocessor returns to STEP 1.

Figure 14:
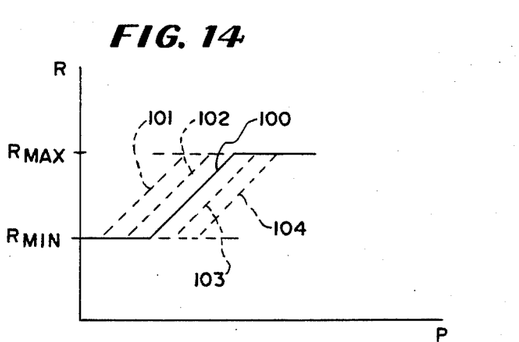
FIG. 14 is a graph of pacer rate versus pressure and shows a family of lines or slopes along which a pacer can function and shows that the rate of change is a function of the difference between pressure at one point in time and pressure at another point in time and not of their absolute value.

In FIG. 14, a number of lines 101-104 parallel to and on either side of the line or graph 100 are programmed in the microprocessor so that the pacer 12 can function along the family of lines 100-104. In this way, the pressure at which rate changes start can be programmed, which is essential because every patient has his/her own resting pressure.

Also, this permits values of pressure to be stored which are greater than $P_{Prog.Max.}$ and less than $P_{Prog. Min.}$.

Suppose for example that $P_{T-1}$ is very high and $R_{T-1}$ is at $R_{Max.}$. If $P_T$ is smaller, then $R_{T-1}$ is permitted to decrease along the sloped line 100 for the mode of operation outlined in the flow chart shown in FIG. 15.

Figures 16, 17:
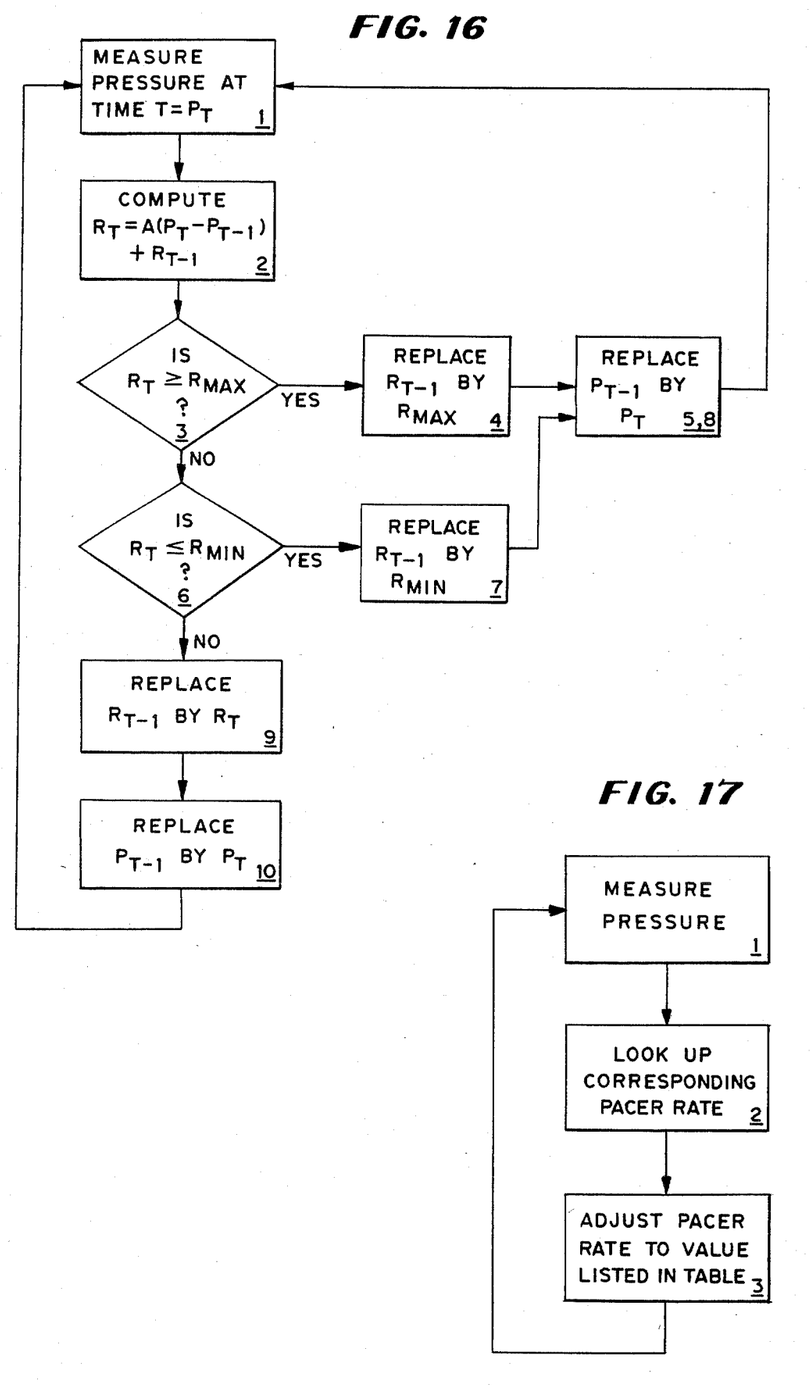
FIG. 16 is a flow chart of the program or routine carried out by the control circuitry (e.g. microprocessor) of the apparatus shown in FIG. 1 and is modified from the flow chart shown in FIG. 15 to permit values of pressure to be stored which are greater than the preprogrammed maximum pressure and less than the preprogrammed minimum pressure to establish the family of lines or slopes along which the pacer can function as shown in FIG. 14 so that the apparatus will not be sensitive to drift of the pressure sensor.
FIG. 17 is a flow chart of a program or routine carried out by the control circuitry of the apparatus shown in FIG. 1 which uses a look-up table suitable for both linear and non-linear relationships between heart rate or pacer rate and pressure.

In the flow chart shown in FIG. 16, the STEPS 1-10 are essentially the same as STEPS 1-10 in the flow chart shown in FIG. 15. However, STEPS 5 and 8 have been modified from STEPS 5 and 8 in the flow chart shown in FIG. 15 and this permits values of pressure to be stored which are greater than $P_{Prog.Max.}$ and less than $P_{Prog.Min.}$.

For the mode of operation defined by the flow chart shown in FIG. 16, $P_{Prog.Max.}$ and $P_{Prog.Min.}$ have no meaning.

In STEP 5 and in STEP 8 combined, $P_T$ is stored as $P_{T-1}$. Also note that STEP 10 can be combined with STEPS 5 and 8.

In FIG. 17 there is set forth a simple flow chart which utilizes a look-up table of right ventricular systolic pressure versus heart/pacer rate suitable for both linear and non-linear relationships between pacer/rate and pressure.

The steps of this program or routine are as follows:

STEP 1. Here pressure is measured.

STEP 2. Here the corresponding pacer rate is pulled from the look-up table stored in memory. Each pressure reading or range of pressure readings has a corresponding rate which had previously been entered into the memory.

STEP 3. Here the pacer rate is adjusted or changed to that one found in the memory which corresponds to the measured value of pressure.

After STEP 3, the microprocessor loops back to STEP 1 and continues to monitor the pressure. In this program or routine, no compensation is provided for sensor drift.

Figure 18:
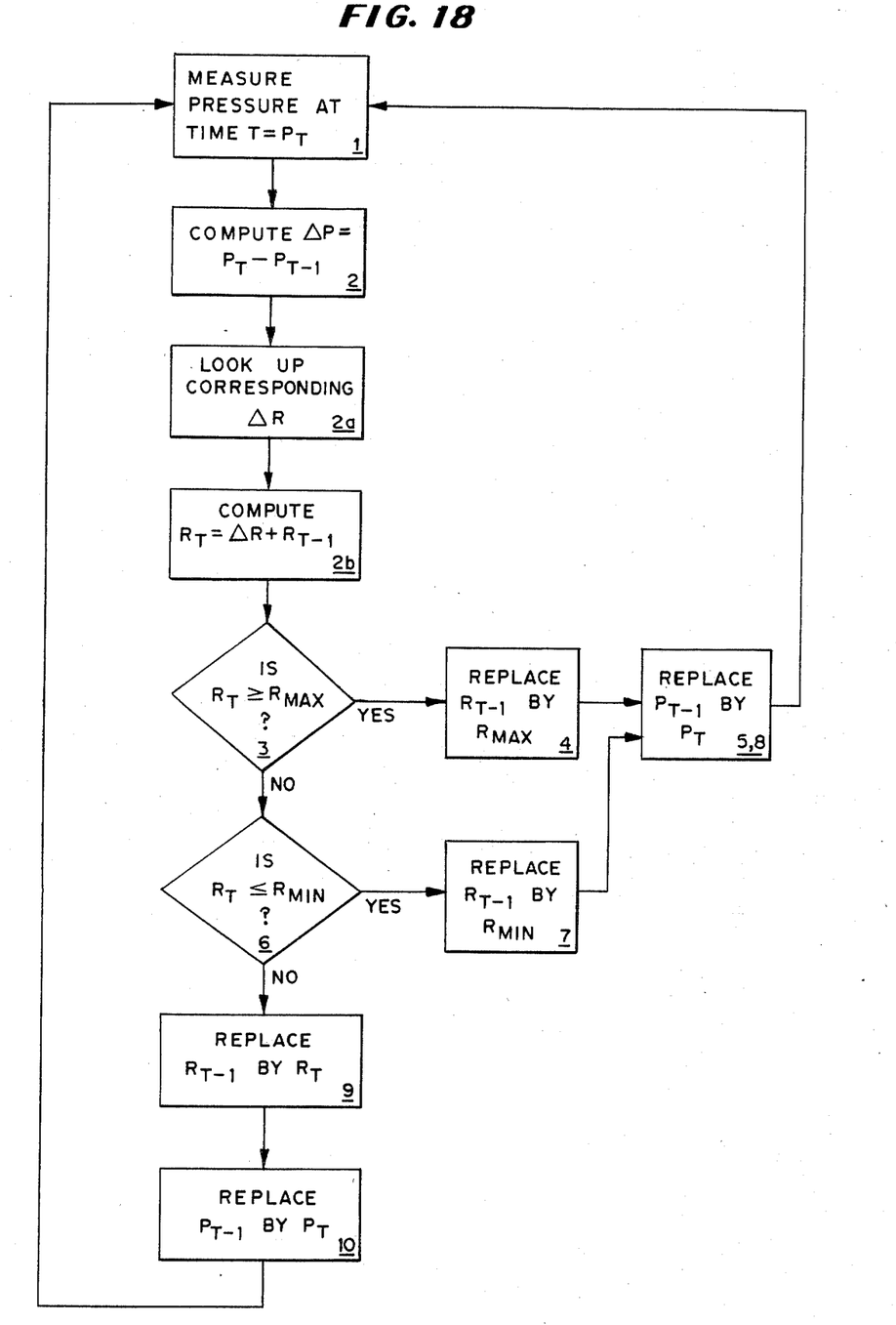
FIG. 18 is a flow chart similar to the flow chart shown in FIG. 16 of a program or routine carried out by the control circuitry of the apparatus shown in FIG. 1 using a look-up table for the change in pressure and not the actual value of the pressure so that the apparatus will not be sensitive to drift of the pressure sensor.

In FIG. 18 is illustrated a flow chart of another program or routine which is analogous to the routine and flow chart therefor shown in FIG. 16. In this routine, compensation for sensor drift is provided by using a look-up table for the change in pressure and not the actual value of the pressure (right ventricular systolic pressure). The steps of this program are as follows:

STEP 1. Here the pressure is measured at time T to determine $P_T$.

STEP 2. Here the microprocessor computes $\Delta P = P_T - (P_{T-1})$ which is the change in pressure.

STEP 2a. Here the microprocessor looks up in the memory the corresponding pacer rate change, $\Delta R$ (which can be a function of $R_{T-1}$, the present rate).

STEP 2b. Here the microprocessor computes $R_T = \Delta R + R_{T-1}$.

STEPS 3-10. These steps are identical to steps 3-10 of the flow chart shown in FIG. 16.

In any one of the programs represented by the flow charts in FIGS. 15-18, the pacer rate changes may be smoothed by smoothing the changes in pressure. This can be done in several ways.

One approach is to compute the sign of the result of $\Delta P_T = P_T - (P_{T-1})$ when $P_T$ is measured and compare the sign (positive or negative) to the sign of the N−1 previously computed differences which have been stored in the memory. If no sign change has occurred in N consecutive samples, the algorithm proceeds to determine the appropriate rate change.

Figure 19:
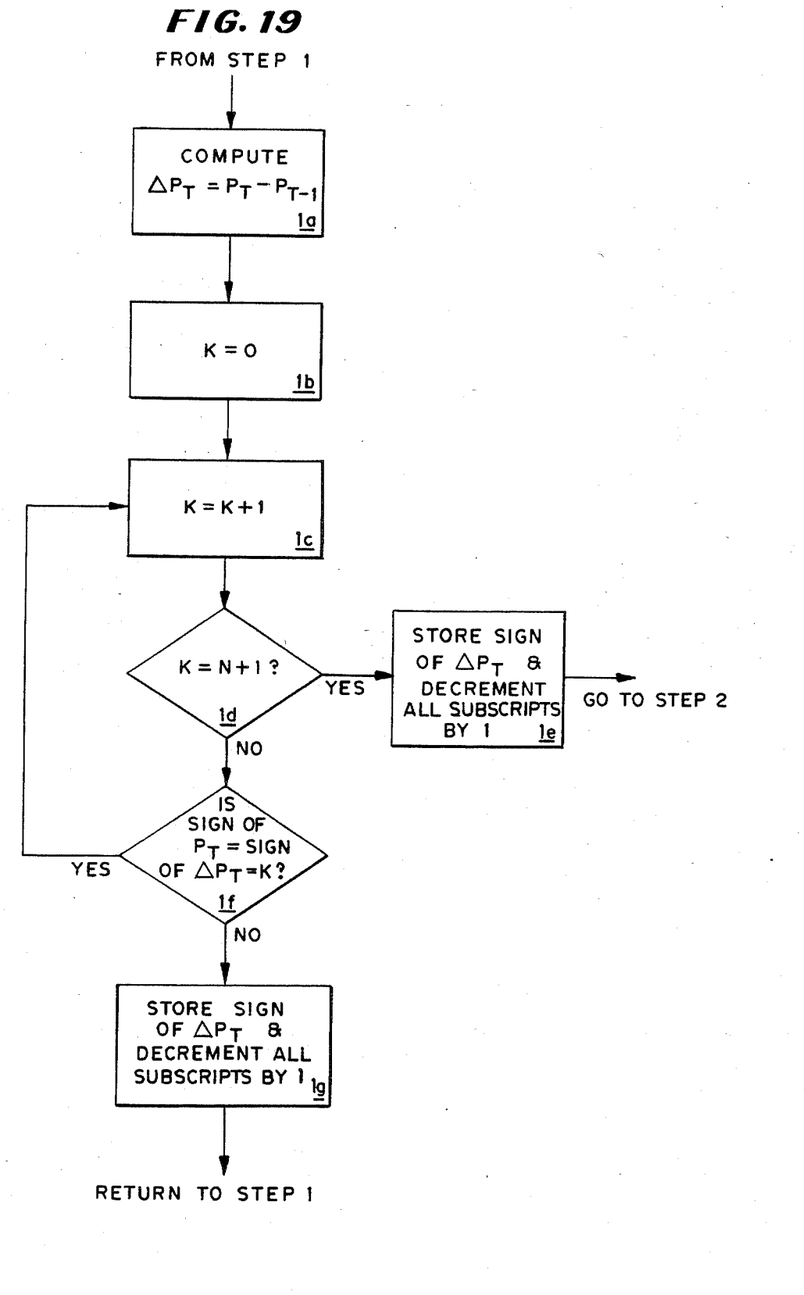
FIG. 19 is a flow chart of a subroutine that can be carried out by the control circuitry of the apparatus shown in FIG. 1 to provide smoothing of the heart rate changes by smoothing the changes in pressure and is inserted between the first step and the second step of the routine or program shown in any one of FIGS. 15, 16, 17 and 18.

This is done with a subroutine shown in FIG. 19 which is inserted between STEPS 1 and 2 in any one of the flow charts shown in FIGS. 15-18. The steps followed in this subroutine are as follows:

STEP 1a. Here $\Delta P_T$ is computed.

STEPS 1b–1d. These steps define a counting loop for indexing the subscripts of the previously calculated ΔP's stored in the memory of the microprocessor.

STEP 1e. If K=N+1 at STEP 1d, at STEP 1e, the sign of $P_T$ is stored and all subscripts are decremented by 1. Then, the microprocessor or algorithm carried out therein goes to STEP 2.

STEP 1f. If K≠N+1 at STEP 1d, at STEP 1f, a determination of the sign of the present ΔP is made to see if it is equal to that of one of the previous N−1 ΔP's.

If the answer is yes, the microprocessor loops back to STEP 1c to increment to ΔP for the next comparison.

STEP 1g. If the sign of the present ΔP is not equal to that of one of the previous N−1ΔP's, the sign of the present ΔP is stored and all stored signs are moved down one level in the memory stack having a height N−1. Then the microprocessor returns to STEP 1.

Again, if N−1 comparisons have been made without any sign changes occurring such that the answer at STEP 1d is yes, at STEP 1e the sign of ΔP is stored, the stack is moved down and the microprocessor proceeds to STEP 2 for an appropriate pacer rate change based upon $\Delta P_T$.

Another approach to smoothing would be to use the subroutine shown in FIG. 19 except to change the pacer rate based upon the average value of ΔP over the N most recent samples if no sign change has occurred.

From the foregoing description, it will be apparent that the apparatus 10 of the present invention and the method for using same described above have a number of advantages, some of which have been described above and others of which are inherent in the invention. In particular, the apparatus 10 allows an implanted pacer system to mimic a change in heart rate that would normally occur in a healthy heart when the individual is exercising and his heart is not naturally changing the pacing rate thereof due to some heart malfunction such as sinus node disease. Such apparatus or pacer system 10 will have very little time lag relative to the exercise activity and responds quickly to a need for a changed pacer rate.

Also it will be apparent that modifications can be made to the apparatus 10 and method for using same without departing from the teachings of the present invention. Accordingly, the scope of the invention is only to be limited as necessitated by the accompanying claims.

We claim:

1. An apparatus for pacing a heart in accordance with the heart/pacer rate needed to produce a required cardiac output while the person is exercising, comprising:
    a pacer adapted to be implanted in a human body and having a pulse generator and control circuitry therein;
    a pacing lead adapted to be implanted in a heart and having a distal electrode adapted to engage and supply pacing pulses to a right ventricle of a heart;
    pressure sensing means mounted on said pacing lead for sensing right ventricular systolic pressure; and
    said control circuitry further including means for relating said sensed right ventricular systolic pressure and/or the time derivative thereof with the required rate needed to supply a desired cardiac output and for causing said pacer to pace the heart at the required rate when the heart is not naturally paced.

2. The apparatus of claim 1 wherein said pressure sensing means comprise a strain gauge.

3. The apparatus of claim 1 wherein said pressure sensing means comprise a piezo-resistive microelectronic pressure transducer.

4. The apparatus of claim 3 wherein said pacing lead has a proximal terminal electrode assembly thereon and four insulated sensor wire conductors therein, said sensor wire conductors being coupled between said pressure transducer and said proximal terminal electrode assembly.

5. The apparatus of claim 4 wherein said proximal terminal electrode assembly includes a generally cylindrical body, a central proximal cathode terminal pin which extends rearwardly from said body and four smaller pins parallel to and spaced from and extending rearwardly parallel to said central cathode terminal pin from said body, said four sensor wire conductors being connected respectively to said four pins.

6. The apparatus of claim 4 wherein said lead includes a tubular sheath and a coiled wire conductor therein coupled between said distal electrode of said pacing lead and said proximal terminal electrode assembly, and said four sensor wire conductors are coiled with and between coils of said coiled wire conductor so as not to obstruct the lumen within the coiled conductor which lumen is adapted to receive a stylet therethrough.

7. The apparatus of claim 4 wherein said pacing lead includes a tubular sheath and a coiled wire conductor therein coupled between said distal electrode and said proximal terminal electrode assembly, and said four sensor wire conductors extend within said sheath parallel to the axis thereof and between said coiled wire conductor and said sheath so as not to obstruct the lumen within the coiled conductor which lumen is adapted to receive a stylet therethrough.

8. The apparatus of claim 3 wherein said proximal terminal electrode assembly includes a generally cylindrical body, a central cathode terminal pin extending rearwardly from said body and four spaced apart conductive rings on said body, said four sensor wire conductors being connected, respectively, to said four conductive rings.

9. The apparatus of claim 3 wherein said control circuitry includes a microprocessor programmed to supply voltage pulses to said pressure transducers for pressure sampling to minimize the power drain of the pressure transducer on the power supply of the pacer.

10. The apparatus of claim 9 wherein said voltage pulses have a duty cycle of at least 1:200.

11. The apparatus of claim 1 wherein said control circuitry further includes a microprocessor and said means for relating the right ventricular systolic pressure and/or the time derivative thereof with the required rate through the implementation of a stored algorithm.

12. The apparatus of claim 11 wherein said microporocessor further comprises means for implementing said algorithm including means for:
    measuring the pressure in the right ventricle at a point in time T;
    computing the heart/pacer rate $R_T$ from a programmed slope "A" of a graph of heart rate versus pressure between a minimum heart rate and a maximum heart rate;
    determining whether the heart rate calculated is equal to or above the maximum programmed pacer rate or equal to or below the minimum programmed pacer rate; and
    if the calculated heart rate is at or above the maximum programmed pacer rate or at or below the minimum programmed pacer rate, replacing the pacer rate value stored in the memory of the microprocessor with either the maximum programmed pacer rate or the minimum programmed pacer rate respectively; or, if the calculated heart rate is between the minimum heart rate and the maximum programmed pacer rate, replacing the pacer rate value stored in the memory with the newly calculated heart rate in the memory of the microprocessor;

replacing the pressure value stored in the memory of the microprocessor at time $T-1$ with the newly measured pressure value; and altering the pacer rate of the pacer by the newly calculated heart rate.

13. The apparatus of claim 12 wherein the algorithm programmed in said microprocessor includes a family of slopes parallel to the first named slope whereby the algorithm defined in claim 12 will function independent of absolute pressure and in response to changes in pressure so as to be substantially insensitive to drift in the pressure sensing means.

14. The apparatus of claim 11 wherein said microprocessor further includes memory means comprising look-up table of required pacing rates relative to various values of right ventricular systolic pressure and means for implementing said algorithm including means for:

measuring the pressure in the right ventricle;

looking up the corresponding heart rate in the look-up table;

adjusting the pacer rate to the value looked up in the look-up table; and monitoring and repeating the step of measuring pressure and changing the pacing rate as the pressure changes.

15. The apparatus of claim 11 wherein said microprocessor further includes memory means comprising a look-up table of required heart rate changes relative to various values of right ventricular systolic pressure changes and means for implementing said algorithm including means for:

measuring the pressure at a first point in time;

computing the incremental change in pressure, $\Delta P = P_T - (P_{T-1})$;

looking up the corresponding $\Delta R$ in the look-up table;

computing the required heart rate $R_T = \Delta R + (R_{T-1})$;

determining whether the computed heart rate is equal to or above the maximum programmed pacer rate or is equal to or below the minimum programmed pacer rate; and if the calculated heart rate meets either of these conditions, replacing the pacer rate $R_{T-1}$ by either the maximum programmed pacer rate or minimum programmed pacer rate stored in the memory of the microprocessor and replacing the last sensed pressure value with the newly sensed pressure value;

if the heart rate calculated is between the maximum and minimum pacer rates stored in the memory of the microprocessor, replacing the last pacing rate by the newly computed heart rate and replacing the last pressure value by the newly measured pressure value; and adjusting the pacer rate to the value of the heart rate just calculated.

16. The apparatus of claim 15 wherein the heart/pacer rate changes are smoothed by smoothing the changes in pressure.

17. The apparatus of claim 15 wherein the sign of the result of $\Delta P_T = P_T - (P_{T-1})$ is compared to the sign of the $N-1$ previously computed differences which have been stored and if there is no sign change in N consecutive samples, the algorithm proceeds to determine the appropriate rate change, if the sign of the present increment in pressure $\Delta P$ is equal to the sign of the previous $N-1$ increments in pressure, the algorithm increments another increment of pressure $\Delta P$ for the next comparison, and if the sign changes, the new sign is stored in the memory and the algorithm returns to the initial step of measuring pressure.

18. The apparatus of claim 15 wherein the rate change is based on the average value of $\Delta P$ over the N most recent samples if no sign change has occurred.

19. A method for pacing a heart in accordance with the heart rate needed to produce a required cardiac output while the person is exercising comprising the steps of:

sensing right ventricular systolic pressure;

relating the right ventricular systolic pressure and/or the time derivative thereof with the required heart rate needed to supply a desired cardiac output; and pacing the heart at the required heart rate when the heart is not naturally paced.

20. The method of claim 19 wherein said right ventricular systolic pressure is sensed by a piezo-resistive pressure transducer.

21. The method of claim 20 including the step of supplying voltage pulses to said pressure transducer for pressure sampling to minimize the power drain of the pressure transducer on a power supply for the transducer.

22. The method of claim 21 wherein said voltage pulses have a duty cycle of at least 1:200.

23. The method of claim 19 wherein said steps of relating the right ventricular systolic pressure and/or the time derivative thereof with the required heart rate comprises the steps of:

measuring the pressure in the right ventricle at a point in time T;

computing the heart rate $R_T$ from a slope "A" of a graph of heart rate versus pressure between a minimum programmed pacer rate and a maximum programmed pacer rate;

determining whether the heart rate calculated is equal to or above the maximum programmed pacer rate or equal to or below the minimum programmed pacer rate; and if the calculated heart rate is at or above the maximum programmed pacer rate or at or below the minimum programmed pacer rate, replacing the pacer rate value stored in the memory with either the maximum programmed pacer rate or the minimum programmed pacer rate; or if the calculated heart rate is between the minimum programmed pacer rate and the maximum programmed pacer rate, replacing the pacer rate value stored in a memory with the newly calculated heart rate in the memory;

replacing the pressure value stored in the memory at time $T-1$ with the newly measured pressure value; and altering the pacer rate of the pacer by the newly calculated heart rate.

24. The method of claim 23 wherein the heart rate is computed from a family of slopes parallel to the first named slope whereby said method is independent of absolute pressure and alters pacer rate in response to changes in pressure so as to be substantially insensitive to drift in any pressure sensor used for sensing pressure.

25. The method of claim 23 wherein said step of relating the right ventricular systolic pressure and/or the time derivative thereof with the required heart rate comprises the steps of:

measuring the pressure at a first point in time;

computing the incremental change in pressure, $\Delta P = P_T - (P_{T-1})$;

looking up the corresponding $\Delta R$ in a look-up table of heart rates relative to various values of right ventricular systolic pressure;

computing the required heart rate $R_T = \Delta R + (R_{T-1})$;

determining whether the computed heart rate is equal to or above the maximum programmed pacer rate or is equal to or below the minimum programmed pacer rate; and if the calculated heart rate meets either of these conditions, replacing the pacer rate $R_{T-1}$ by either the maximum programmed pacer rate or minimum programmed pacer rate stored in a memory and replacing the last sensed pressure value with the newly sensed pressure value;

if the heart rate calculated is between the maximum and minimum programmed pacer rates stored in a memory, replacing the last pacing rate by the newly computed heart rate and replacing the last pressure value by the newly measured pressure value; and adjusting the pacer rate to the value of the pacer rate just calculated.

26. The method of claim 25 wherein the heart rate changes are smoothed by smoothing the changes in pressure.

27. The method of claim 26 wherein the sign of the result, $\Delta P_T = P_T - (P_{T-1})$ is compared to the sign of the $N-1$ previously computed differences which have been stored and if there is no sign change in N consecutive samples, determining the appropriate rate change, if the sign of the present increment in pressure $\Delta P$ is equal to the sign of the previous $N-1$ increments in pressure, incrementing another increment of pressure $\Delta P$ for the next comparison, and if the sign changes, storing the new sign in the memory and returning to the initial step of measuring pressure.

28. The method of claim 27 wherein the rate change is based on the average value of $\Delta P$ over the N most recent samples if no sign change has occurred.

29. The method of claim 19 wherein said step of relating the right ventricular systolic pressure and/or the time derivative thereof with the required heart rate comprises the steps of:

measuring the pressure in the right ventricle;

looking up the corresponding heart rate in a look-up table of heart rates relative to various values of right ventricular systolic pressure;

adjusting the pacer rate to the value looked up in the look-up table; and monitoring and repeating the step of measuring pressure and changing the pacing rate as the pressure changes.

* * * * *

UNITED STATES PATENT AND TRADEMARK OFFICE
CERTIFICATE OF CORRECTION

PATENT NO.   :   4,566,456

DATED        :   January 28, 1986

INVENTOR(S)  :   GERRIT KONING, ET AL

It is certified that error appears in the above-identified patent and that said Letters Patent is hereby corrected as shown below:

Column 7, line 66, "AR" should be --$\Delta$R--.

Signed and Sealed this

Eleventh Day of November, 1986

Attest:

DONALD J. QUIGG

Attesting Officer         Commissioner of Patents and Trademarks